United States Patent
Hansen

(10) Patent No.: US 10,773,003 B2
(45) Date of Patent: Sep. 15, 2020

(54) SYSTEM ARCHITECTURE THAT ALLOWS PATIENT REPLACEMENT OF VAD CONTROLLER/INTERFACE MODULE WITHOUT DISCONNECTION OF OLD MODULE

(71) Applicant: TC1 LLC, St. Paul, MN (US)

(72) Inventor: John Freddy Hansen, Pleasanton, CA (US)

(73) Assignee: TCI LLC, St. Paul, MN (US)

(*) Notice: Subject to any disclaimer, the term of this patent is extended or adjusted under 35 U.S.C. 154(b) by 185 days.

(21) Appl. No.: 15/980,896

(22) Filed: May 16, 2018

(65) Prior Publication Data
US 2018/0256796 A1    Sep. 13, 2018

Related U.S. Application Data

(63) Continuation of application No. PCT/US2016/062023, filed on Nov. 15, 2016.
(Continued)

(51) Int. Cl.
*A61N 1/362*    (2006.01)
*A61M 1/10*    (2006.01)
*A61M 1/12*    (2006.01)

(52) U.S. Cl.
CPC .......... *A61M 1/1086* (2013.01); *A61M 1/101* (2013.01); *A61M 1/122* (2014.02);
(Continued)

(58) Field of Classification Search
CPC .... A61M 1/1086; A61M 1/101; A61M 1/122; A61M 2205/16–18
See application file for complete search history.

(56) References Cited

U.S. PATENT DOCUMENTS 3,882,861 A    5/1975    Kettering
4,521,871 A    6/1985    Galdun et al.
(Continued)

FOREIGN PATENT DOCUMENTS

EP    1 812 094 A    5/2006
WO    2006/055745 A2    5/2006
(Continued)

OTHER PUBLICATIONS

Heartmate II , "The HeartMate II system", HeartMate II, Left Ventricular Assist System, Retrieved from Internet : http://heartmateii.com/heartmate-ii-system.aspx, Jul. 16, 2015, 2 pages.
(Continued)

*Primary Examiner* — Mallika D Fairchild
(74) *Attorney, Agent, or Firm* — Kilpatrick Townsend & Stockton LLP

(57) ABSTRACT

Mechanical circulatory assist systems and related methods accommodate the connection of a second patient interface module used to control a circulatory assist pump without having to disconnect a first patient interface module used to control the circulatory assist pump. A mechanical circulatory assist system includes a blood pump, a first patient interface module, and a first connector. The first patient interface module is operatively coupled with the blood pump and configured to control operation of the blood pump. The first connector is operatively coupled with the blood pump and configured to couple with a second patient interface module configured to control operation of the blood pump without decoupling of the first interface module from the blood pump.

23 Claims, 11 Drawing Sheets

Related U.S. Application Data

(60) Provisional application No. 62/258,035, filed on Nov. 20, 2015.

(52) U.S. Cl.
CPC ..... *A61M 2205/16* (2013.01); *A61M 2205/17* (2013.01); *A61M 2205/18* (2013.01)

(56) References Cited

U.S. PATENT DOCUMENTS

| | | | |
|---|---|---|---|
| 5,046,965 A | 9/1991 | Neese et al. |
| 5,695,474 A | 12/1997 | Daugherty |
| 5,888,242 A | 3/1999 | Antaki et al. |
| 5,935,105 A | 8/1999 | Manning et al. |
| 5,991,595 A | 11/1999 | Romano et al. |
| 6,071,093 A | 6/2000 | Hart |
| 6,116,862 A | 9/2000 | Rau et al. |
| 6,146,179 A | 11/2000 | Denny et al. |
| 6,183,412 B1 | 2/2001 | Benkowski et al. |
| 6,234,772 B1 | 5/2001 | Wampler et al. |
| 6,264,635 B1 | 7/2001 | Wampler et al. |
| 6,494,736 B2 | 12/2002 | Mito et al. |
| 6,592,620 B1 | 7/2003 | Lancisi et al. |
| 6,688,861 B2 | 2/2004 | Wampler |
| 7,340,304 B2 | 3/2008 | MacDonald et al. |
| 7,425,142 B1 | 9/2008 | Putz et al. |
| 7,658,613 B1 | 2/2010 | Griffin et al. |
| 7,699,586 B2 | 4/2010 | Larose et al. |
| 7,961,156 B2 | 6/2011 | Knott et al. |
| 7,976,271 B2 | 7/2011 | Larose et al. |
| 7,997,854 B2 | 8/2011 | Larose et al. |
| 8,007,254 B2 | 8/2011 | Larose et al. |
| 8,029,441 B2 | 10/2011 | Mazza et al. |
| 8,152,493 B2 | 4/2012 | Larose et al. |
| 8,157,720 B2 | 4/2012 | Marseille et al. |
| 8,186,665 B2 | 5/2012 | Akema |
| 8,323,174 B2 | 12/2012 | Jeevanandam et al. |
| 8,344,847 B2 | 1/2013 | Moberg et al. |
| 8,348,678 B2 | 1/2013 | Hardisty et al. |
| 8,449,444 B2 | 5/2013 | Poirier |
| 8,506,471 B2 | 8/2013 | Bourque |
| 8,562,508 B2 | 10/2013 | Dague et al. |
| 8,597,350 B2 | 12/2013 | Rudser et al. |
| 8,628,460 B2 | 1/2014 | Yomtov et al. |
| 8,639,348 B2 | 1/2014 | Geheb |
| 8,652,024 B1 | 2/2014 | Yanai et al. |
| 8,657,733 B2 | 2/2014 | Ayre et al. |
| 8,668,473 B2 | 3/2014 | Larose et al. |
| 8,684,763 B2 | 4/2014 | White et al. |
| 8,894,561 B2 | 11/2014 | Callaway et al. |
| 8,971,958 B2 | 3/2015 | Frikart et al. |
| 9,302,035 B2 | 4/2016 | Flaherty et al. |
| 2002/0007198 A1 | 1/2002 | Haupert et al. |
| 2005/0071001 A1 | 3/2005 | Jarvik |
| 2007/0078293 A1 | 4/2007 | Shambaugh et al. |
| 2007/0142696 A1 | 6/2007 | Crosby et al. |
| 2008/0021394 A1 | 1/2008 | Larose et al. |
| 2009/0118827 A1 | 5/2009 | Sugiura |
| 2009/0203957 A1 | 8/2009 | Larose et al. |
| 2011/0218383 A1 | 9/2011 | Broen et al. |
| 2012/0046514 A1 | 2/2012 | Bourque |
| 2012/0095281 A1 | 4/2012 | Reichenbach et al. |
| 2012/0172657 A1 | 7/2012 | Marseille et al. |
| 2012/0183261 A1 | 7/2012 | Schwandt et al. |
| 2013/0096364 A1 | 4/2013 | Reichenbach et al. |
| 2013/0121821 A1 | 5/2013 | Ozaki et al. |
| 2013/0127253 A1 | 5/2013 | Stark et al. |
| 2013/0170970 A1 | 7/2013 | Ozaki et al. |
| 2013/0225909 A1 | 8/2013 | Dormanen et al. |
| 2013/0314047 A1 | 11/2013 | Eagle et al. |
| 2014/0073838 A1 | 3/2014 | Dague et al. |
| 2014/0194985 A1 | 7/2014 | Vadala, Jr. |
| 2014/0243970 A1 | 8/2014 | Yanai |
| 2014/0309733 A1 | 10/2014 | Cotter et al. |
| 2015/0038771 A1 | 2/2015 | Marseille et al. |
| 2016/0095968 A1 | 4/2016 | Rudser |
| 2018/0250459 A1 | 9/2018 | Kimball et al. |
| 2018/0256800 A1 | 9/2018 | Conyers et al. |
| 2018/0256801 A1 | 9/2018 | Conyers et al. |

FOREIGN PATENT DOCUMENTS

| | | |
|---|---|---|
| WO | 2010122139 A1 | 10/2010 |
| WO | 2011081626 A1 | 7/2011 |
| WO | 2014107424 A2 | 7/2014 |
| WO | 2015017770 A1 | 2/2015 |
| WO | 2017087717 A1 | 5/2017 |
| WO | 2017087728 A1 | 5/2017 |
| WO | 2017087785 A1 | 5/2017 |

OTHER PUBLICATIONS

My LVAD , "Berlin Heart Incor", Retrieved from Internet:http://www.mylvad.com/content/berlin-heart-incor, Jul. 16, 2015, 3 pages.

SYSTEM ARCHITECTURE THAT ALLOWS PATIENT REPLACEMENT OF VAD CONTROLLER/INTERFACE MODULE WITHOUT DISCONNECTION OF OLD MODULE

CROSS-REFERENCE TO RELATED APPLICATION

The present application is a Continuation of PCT/US2016/062023 filed Nov. 15, 2016; which claims priority to and benefit of U.S. Provisional Application No. 62/258,035, filed Nov. 20, 2015, the disclosure of which is incorporated herein by reference in its entirety for all purposes.

BACKGROUND

Ventricular assist devices, known as VADs, often include an implantable blood pump and are used for both short-term (i.e., days, months) and long-term applications (i.e., years or a lifetime) where a patient's heart is incapable of providing adequate circulation, commonly referred to as heart failure or congestive heart failure. According to the American Heart Association, more than five million Americans are living with heart failure, with about 670,000 new cases diagnosed every year. People with heart failure often have shortness of breath and fatigue. Years of living with blocked arteries and/or high blood pressure can leave a heart too weak to pump enough blood to the body. As symptoms worsen, advanced heart failure develops.

A patient suffering from heart failure may use a VAD while awaiting a heart transplant or as a long term destination therapy. A patient may also use a VAD while recovering from heart surgery. Thus, a VAD can supplement a weak heart (i.e., partial support) or can effectively replace the natural heart's function.

A VAD system often includes a controller or patient interface module to control operation of the VAD. The patient interface module can provide operational feedback to the user such as system status indications (e.g., battery charge status) and system alarms (e.g., for system faults).

A fault in a patient interface module may sometimes require replacing the faulty patient interface module with another (typically identical) patient interface module. When the fault is critical or otherwise appears to require urgent replacement, the replacement may need to be performed by the patient or a caregiver, as opposed to a perceived non-critical fault when the replacement can be delayed until the patient visits a clinic. Replacing a patient interface module, whether the fault is critical or not, can be a life-and-death situation for the patient. The patient/caregiver typically understands what is at stake and perceives the replacement as a very high-stress operation. The combination of high stress and a very rare situation (for which training, if any, may have been conducted a long time ago) can lead to user error during replacement, resulting in adverse events, including even possible patient death by inadvertent disconnection of modules which supply power to the pump.

Some progress has been made in reducing adverse consequences associated with patient replacement of a faulty patient interface module. For example, patient interface module connectors can include clearly marked labels that indicate how to make the connection. Ideally, a VAD system is configured to minimize faults requiring replacement of a faulty patient interface module. Conventional mechanical circulatory support (MCS) systems, however, are still configured to allow only one controller supplying power to be connected to the VAD at a time. Thus, replacement of the controller interface module requires following carefully designed steps to ensure that no power is lost at any point in the replacement process.

While some progress has been made, existing approaches have some undesirable attributes. Typical approaches focus on patient training, designing the interface modules to prohibit improper connections, and visual markings and cues. None of these fully address the underlying problem. For example, even when clearly marked, patient interface module connectors are typically difficult to connect, partly due to construction (patient interface module connectors need to be difficult to accidentally disconnect, large enough for limited dexterity patients to handle, etc.) and partly due to lack of recent training of the patient in replacing a faulty patient interface module. Patient training on how to replace a faulty patient interface module is typically infrequent so as to occur long before a "live" replacement situation. More so, consistent training cannot adequately prepare all patients for performing the operations in a stressful emergency situation. Even if the occurrence of faults requiring the replacement of a patient interface module are minimized, the act of replacing a faulty patient interface module is not any easier for the patient to accomplish and in fact may be harder due to the reduced resulting patient experience with replacing a faulty patient interface module. Accordingly, improved approaches and systems for replacing a faulty patient interface module would be beneficial.

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

Mechanical circulatory assist systems, and related methods, include a connector to which a replacement patient interface module can be coupled without having to remove a faulty patient interface module. For example, each patient interface module can include a connector to which an additional patient interface module can be connected. In many embodiments, the system architecture allows for one, two, or more than two patient interface modules to be connected simultaneously. In many embodiments, the system is configured to transfer control of one or more blood pumps from the faulty patient interface module to the replacement patient interface module. For example, the replacement and faulty patient interface modules can be configured to negotiate control of the one or more blood pumps. As another example, each of the patient interface modules can be configured to detect a critical fault requiring replacement, generate an alarm to the user to replace the patient interface module, and invoke a slave mode so as to accept the replacement patient interface module as the master. Because several patient interface modules can be connected simultaneously, the patient never has to remove one patient interface module before connecting a replacement patient interface module. Not having to remove the faulty patient interface module saves time and also means the patient does not have to go completely without a patient interface module when "replacing" a patient interface module that may still have some functionality. The faulty patient interface module can later be removed from the system under non-urgent conditions by trained staff at a clinic. Moreover, each of the patient interface modules can include one or more battery cells to supply power to the one or more blood pumps. Accordingly, the patient can manage connected battery capacity by connecting and disconnecting patient interface modules, which makes module replacement part of the patient's daily life, and vastly boosts the patient's proficiency in replacing a patient interface module.

Thus, in one aspect, a mechanical circulatory assist system is provided. The mechanical circulatory assist system includes a blood pump, a first patient interface module, and a first connector. The first patient interface module is operatively coupled with the blood pump and configured to control operation of the blood pump. The first connector is operatively coupled with the blood pump and configured to couple with a second patient interface module configured to control operation of the blood pump without decoupling of the first interface module from the blood pump.

One or more of the patient interface modules can include one or more additional features. For example, one or more of the patient interface modules (e.g., the first patient interface module) can include the first connector. The first patient interface module can be configured to detect a fault in the first patient interface module, generate an alarm in response to the detection of the fault in the first patient interface module indicating that the second patient interface module should be coupled with the first connector, and relinquish control of the blood pump to the second patient interface module. The system can include the second patient interface module coupled with the first connector and the second patient interface module can include a second connector configured to couple with a third patient interface module configured to control operation of the blood pump without decoupling of the first and second interface modules from the blood pump. The first patient interface module can include one or more battery cells and be configured to supply power from the one or more battery cells to the blood pump. The system can include the second patient interface module coupled with the first connector and the second patient interface module can include one or more battery cells and be configured to supply power from the one or more battery cells to the blood pump via the first connector. The system can include the second patient interface module coupled with the first connector and the second patient interface module can be configured to detect a fault in the second patient interface module, generate an alarm in response to the detection of the fault in the second patient interface module indicating that the third patient interface module should be coupled with the second connector, and relinquish control of the blood pump to the third patient interface module. The system can include the second patient interface module coupled with the first connector and the first and second patient interface modules can be configured to negotiate control of the blood pump so that one of the first and second patient interface modules functions as a master that controls the operation of the blood pump and the other of the first and second patient interface modules functions as a slave that does not control the operation of the blood pump. The first patient interface module can be configured to detect coupling of the second patient interface module with the first connector and, upon detecting coupling of the second patient interface module with the first connector, transfer control of the blood pump from the first patient interface module to the second patient interface module. The first patient interface module can be configured to detect decoupling of the second patient interface module from the first connector and, upon detecting decoupling of the second patient interface module from the first connector, resume control of the blood pump by the first patient interface module.

The first connector can be included in the system in any suitable location including separate from the first patient interface module. For example, the system can include a percutaneous cable operatively coupling the first patient interface module with the blood pump. The percutaneous cable can include a Y-connector having a first input, a second input, and an output. The first input can operatively couple the first patient interface with the blood pump. The second input can include the first connector. In many embodiments, coupling of the second patient interface module to the first connector operatively decouples the first patient interface module from the blood pump.

The patient interface modules can be configured to negotiate with each other for control of the blood pump. For example, in many embodiments, the system includes the second patient interface module coupled with the first connector and the first and second patient interface modules are configured to negotiate control of the blood pump so that one of the first and second patient interface modules functions as a master that controls the operation of the blood pump and the other of the first and second patient interface modules functions as a slave that does not control the operation of the blood pump.

In many embodiments, the system is configured to accommodate serial connection of one or more external battery modules with the two or more patient interface modules. For example, the system can include an external battery module including a battery output connector, a battery input connector, and one or more battery cells configured to store electrical power. The battery output connector can be configured to be coupled with the first patient interface module input connector and the second patient interface module output connector can be configured to be coupled with the battery input connector so that the external battery module is serially connected between the first and second patient interface modules. At least one of the first and second patient interface module is configured to generate an alert calling for replacement of one of the external battery module in response to a charge level of the external battery module falling below a predetermined level, detect a fault in the first patient interface module, and generate an alert calling for coupling of the second patient interface module with the first connector in response to detecting the fault in the first patient interface module.

The system can include features suitable to a blood pump that is supplied an alternating current. For example, the system can include the second patient interface module coupled with the first connector and each of the first and second patient interface modules can be configured to supply an alternating current to the blood pump. Each of the first and second patient interface modules can include a phase-sensing circuit configured to sense a phase of the alternating current supplied by the respective patient interface module to the blood pump. Each of the first and second patient interface modules can be configured to, upon assuming control of the blood pump from the other of the first and second patient interface modules, supply an alternating current to the blood pump having the same phase as the alternating current that was supplied to the blood pump by the other of the first and second patient interface modules. Instead of a phase-sensing circuit, the second patient interface module can sense when the second patient interface module is connected and seize control of the blood pump. The second patient interface module can be configured to assume control within a very short time period after it has been connected. This time period can be sufficiently long for the second patient interface module to seize control of the blood pump, but too short to have a significant clinical impact on the patient. In many embodiments, the length of time period is a fraction of a second in most cases, but can be up to several seconds long in some cases.

The system can be configured to inhibit patient removal of a patient interface module. For example, the first connector can include a lock configured to lock upon coupling with the second patient interface module to the first connector to prevent decoupling of the second patient interface module from the first connector by a person other than a qualified person. Any suitable configuration can be used to activate the lock. For example, the lock can be configured to be activated mechanically, electrically, and/or through software.

In another aspect, a method is provided for controlling a mechanical circulatory assist system that includes a blood pump. The method includes controlling operation of the blood pump via a first patient interface module operatively coupled with the blood pump, coupling a second patient interface module with a first connector operatively coupled with the blood pump, and transferring control of the blood pump from the first patient interface module to the second patient interface module without decoupling of the first patient interface module from the blood pump.

The method can include adding the second patient interface module upon detection of a fault in the first patient interface module. For example, the method can include detecting a fault condition in the first patient interface module. The method can include generating an alarm in response to the detection of the fault in the first patient interface module indicating that the second patient interface module should be coupled with the first connector.

The method can include automatically transferring control of the blood pump to the second patient interface module upon coupling of the second patient interface with the first connector. For example, the method can include detecting coupling of the second patient interface module with the first connector. The method can include, upon detecting coupling of the second patient interface module with the first connector, transferring control of the blood pump from the first patient interface module to the second patient interface module.

The method can include automatically resuming control of the blood pump by the first patient interface module upon decoupling of the second patient interface module from the first connector. For example, the method can include detecting decoupling of the second patient interface module from the first connector. The method can include, upon detecting decoupling of the second patient interface module from the first connector, resuming control of the blood pump by the first patient interface module.

The method can include coupling any suitable number of patient interface modules with the blood pump. For example, the method can include coupling a third patient interface module to a second connector operatively coupled with the blood pump. The method can include transferring control of the blood pump from the second patient interface module to the third patient interface module without decoupling at least one of the first and second patient interface modules from the blood pump. The method can include detecting a fault condition in the second patient interface module. The method can include generating an alarm in response to the detection of the fault in the second patient interface module indicating that the third patient interface module should be coupled with the second connector.

The method can include supplying electrical power to the blood pump from the first patient interface module and/or the second patient interface module. For example, the method can include supplying electrical power to the blood pump from one or more battery cells included in the first patient interface module and/or supplying electrical power to the blood pump via the first connector from one or more battery cells included in the second patient interface module.

The method can include negotiating control of the blood pump between connected patient interface modules. For example, transferring control of the blood pump from the first patient interface module to the second patient interface module without decoupling of the first patient interface module from the blood pump can include negotiating control of the blood pump between the first and second patient interface modules so that the second patient interface module functions as a master that controls the operation of the blood pump and the first patient interface module functions as a slave that does not control the operation of the blood pump.

In many embodiments of the method, the mechanical circulatory assist system includes a percutaneous cable operatively coupling the first patient interface module with the blood pump. The percutaneous cable can include a Y-connector having a first input, a second input, and an output. The first input can operatively couple the first patient interface with the blood pump. The second input can include the first connector.

In many embodiments of the method, the first patient interface module is automatically operatively decoupled from the blood pump. For example, coupling the second patient interface module to the first connector can operatively decouple the first patient interface module from the blood pump.

In many embodiments of the method, electrical power for powering the blood pump is received via the first connector. For example, the method can include transferring electrical power from an external battery module coupled with the input connector so that the external battery module is serially connected between the first and second patient interface modules.

In many embodiments of the method, an alternating current is supplied to the blood pump. For example, the method can include supplying a first alternating current from the first patient interface module to the blood pump, sensing a phase of the first alternating current, and supplying a second alternating current from the second interface module to the blood pump so that a phase of the second alternating current matches the phase of the first alternating current.

In many embodiments, the method includes activating a lock upon coupling of the second patient interface module with the first connector to prevent decoupling of the second patient interface module from the first connector by a person other than a qualified person. Any suitable locking mechanism can be used. For example, the lock can be configured to be activated mechanically, electrically, and/or through software.

In another aspect, a mechanical circulatory assist system is provided. The mechanical circulatory assist system includes a blood pump, a first patient interface module, a first connector, and a second patient interface module. The first patient interface module is operatively coupled with the blood pump and configured to control operation of the blood pump. The first connector is operatively coupled with the blood pump and configured to couple with a second patient interface module configured to control operation of the blood pump without decoupling of the first interface module from the blood pump. One or both of the first and second patient interface modules includes protection circuitry configured to prevent back driving of motor drive current into the patient interface module from the other of the first and second patient interface modules. For example, one or both of the first and second patient interface modules can include a diode integrated to block back driving of direct current motor drive current into the patient interface module from the other of the first and second patient interface modules. As another example, the protection circuitry can include any suitable number of isolation switches that can be operated to isolate the patient interface module from back driving of motor drive current into the patient interface module from the other of the first and second patient interface modules.

For a fuller understanding of the nature and advantages of the present invention, reference should be made to the ensuing detailed description and accompanying drawings.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Figure 1:
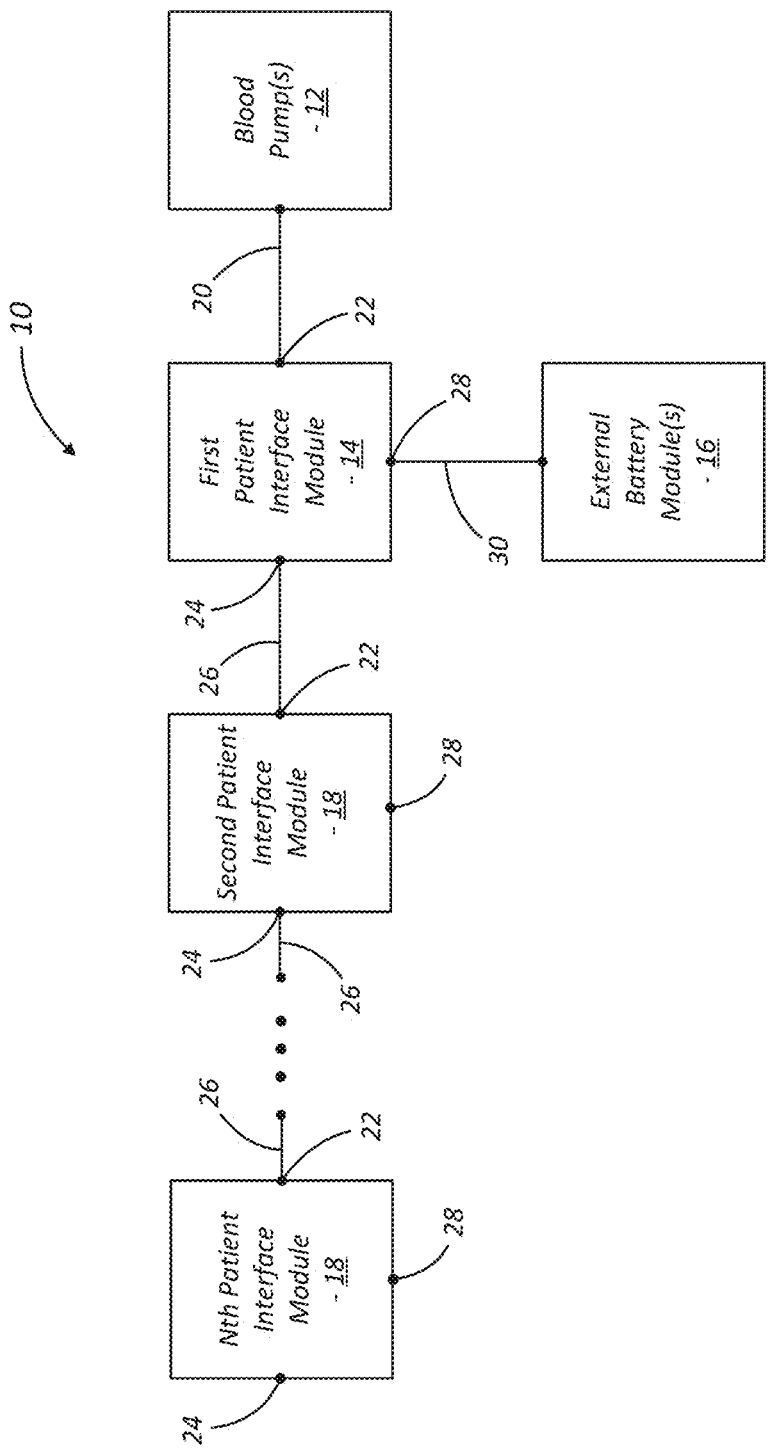
FIG. 1 is a simplified schematic diagram of a mechanical circulatory assist system in which a plurality of patient interface modules can be connected serially, in accordance with many embodiments.

Referring now to the drawings, in which like reference numerals represent like parts throughout the several views, FIG. 1 shows a simplified schematic illustration of a mechanical circulatory assist system 10, in accordance with many embodiments. The mechanical circulatory assist system 10 includes at least one blood pump 12, a first patient interface module 14, and a second patient interface module 18. The system can also include at least one external battery module 16 and/or one or more additional patient interface modules 18. Instead of an external battery module, the system may make use of different power configurations such as a power source coupled to the interface module (internal or external) or other power sources (e.g. supercapacitors). In many embodiments, the blood pump 12 is implanted within a patient. For example, the blood pump 12 can be part of an implanted ventricle assist device (VAD). In many embodiments, the first patient interface module 14 is coupled with the blood pump 12 via a percutaneous cable 20. The interface modules can be configured to direct power from a power source (e.g. battery 16) to the VAD. In the case of a VAD with control electronics, the interface module may provide simple power such as DC power. In the case of a VAD without control electronics, the interface module may provide a drive signal to control operation of the VAD. The external interface modules may also be responsible for data communication with the internal components such as the VAD.

The exemplary system 10 is configured, in part, to address the problem of existing systems, which do not allow for easy replacement of a controller (e.g. interface module) providing life-saving power. One advantage of the exemplary system is the ability to connect a second interface module to maintain power when the first interface module is disconnected. Conventional systems require swift connection of the second, replacement interface module after the first interface module is disconnected. This requires the patient to act quickly in life-dependent circumstances. By contrast, as will be described below, the exemplary system includes redundancy to mitigate this problem. The exemplary system can also include hardware and software to facilitate the hand-off or transfer from the first interface module to the second interface module. A further problem of conventional systems is the lack of an effective and easy way to transfer data (e.g. control or patient data) and settings from the first controller to the replacement controller. These and other problems are addressed by the exemplary system as will be more fully understood from the description herein.

With continued reference to FIG. 1, each of the patient interface modules 14, 18 is configured so that any suitable number of the patient interface modules 14, 18 can be serially connected. Each of the patient interface modules 14, 18 includes an output connector 22 and an input connector 24. The percutaneous cable 20 is coupled with the first patient interface module 14 via the output connector 22 of the first patient interface module. In the illustrated embodiment, the second patient interface module 18 is coupled with the first patient interface module 14 via a connection cable 26, one end of which is coupled with the output connector 22 of the second patient interface module 18 and the other end of which is coupled with the input connector 24 of the first patient interface module 18. One or more additional patient interface modules 18 can be added via the input connector 24 of the second patient interface module 18.

In many embodiments, the second patient interface module 18 can be selectively coupled to the first patient interface module 14 in response to a fault in the first patient interface module 14. For example, a fully-functional first patient interface module 14 can control operation of the blood pump 12 without having the second patient interface module 18 coupled with the first patient interface module 14. In many embodiments, the first patient interface module 14 is configured to monitor the functionality of the first patient interface module 14 and output an alarm (e.g., a visual alarm and/or an audio alarm) to the user of the system 10 when a critical fault in the first patient interface module 14 is detected. If the detected fault in the first patient interface module 14 prevents further safe operation of the blood pump 12 under the control of the first patient interface module 14, the first patient interface module 14 can output an indication that the second patient interface module 18 should be coupled to the input connector 24 of the first patient interface module 14. In many embodiments, the first patient interface module 14 is configured to relinquish control of the blood pump 12 to the second patient interface module 18 upon connection of the second patient interface module 18 to the input connector 24 of the first patient interface module 14. In many embodiments, the first patient interface module 14 is configured to operatively couple respective leads of the connection cable 26 with corresponding leads of the percutaneous cable 20 so that the second patient interface module 18 is operatively coupled with the blood pump 12 in the event of a malfunctioning first patient module 14. One or more additional patient interface modules 18 can be connected via the input connector 24 of the second patient interface module 18 and be configured to operate similarly as described above in response to a fault in the second patient interface module 18.

In many embodiments, the second patient interface module 18 can be selectively coupled to the first patient interface module 14 prior to the occurrence of a fault in the first patient interface module 14. In such embodiments, the blood pump 12 can be controlled by either one of the first and second patient interface modules 14, 18. For example, upon connection of the second patient interface module 18 to the input connector 24 of the first patient interface module 14, the first patient interface module 14 can be configured to relinquish control of the blood pump 12 to the second patient interface module 18. As another example, upon connection of the second patient interface module 18 to the first patient interface module 14, the first patient interface module 14 can continue to control operation of the blood pump 12 and the second patient interface module 14 can operate in a standby mode until the first patient interface module 14 relinquishes control of the blood pump 12 due to, for example, the occurrence of a fault in the first patient interface module 14 that prevents continued safe control of the blood pump 12 by the first patient interface module 14. One or more additional patient interface modules 18 can be connected via the input connector 24 of the second patient interface module 18 and be configured to operate similarly as described above.

In the illustrated embodiment, each of the patient interface modules 14, 18 includes a battery input connector 28 to which one or more external battery modules 16 can be connected in any suitable manner (e.g., via a battery cable 30). Additionally, each of the patient interface modules 14, 18 can include one or more internal battery cells from which power can be supplied to the blood pump 12 and/or one of the patient interface modules 14, 18 connected between the patient interface module and the blood pump 12.

Figure 2:
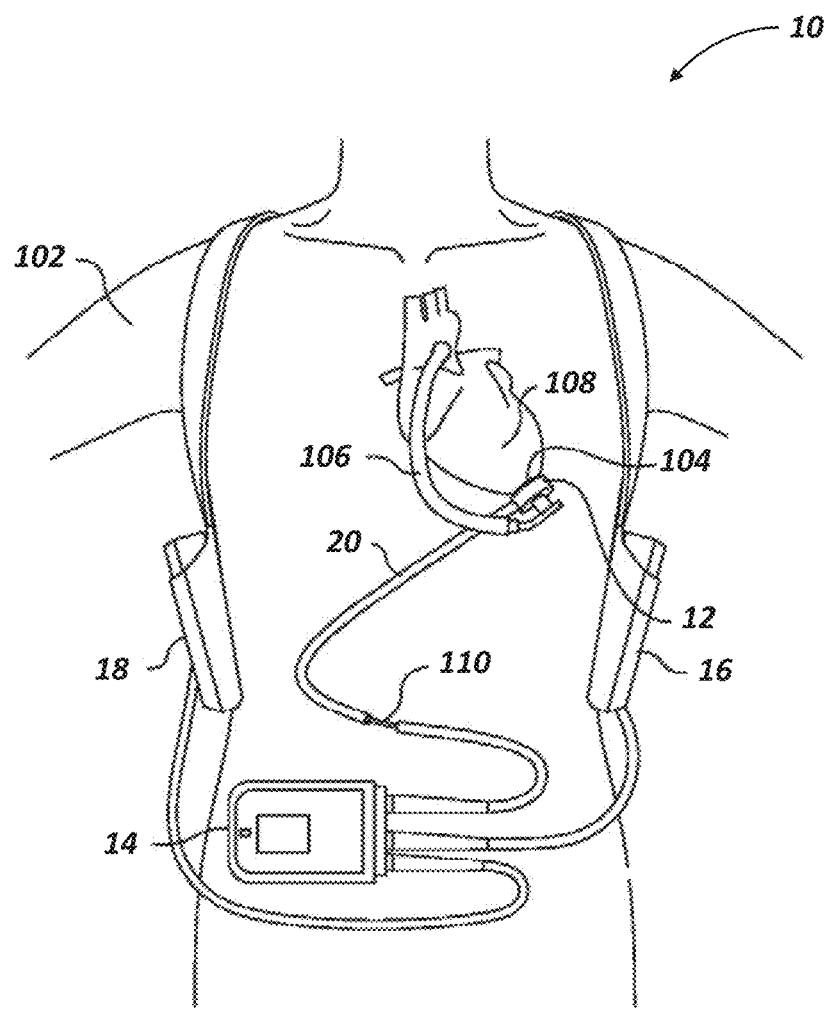
FIG. 2 illustrates an example embodiment of the mechanical circulatory assist system of FIG. 1.

FIG. 2 illustrates an example embodiment of the mechanical circulatory support system 10. In the illustrated embodiment, the mechanical circulatory support (MCS) system 10 includes a ventricular assist device (VAD) (i.e., blood pump 12) implanted in a patient 102, a ventricular cuff 104, an outflow cannula 106, a first patient interface module 14, an external battery module 16, and a second patient interface module 18 coupled with the first patient interface module 14. The VAD 12 can be attached to an apex of the left ventricle, as illustrated, or the right ventricle, or both ventricles of the patient's heart 108. The VAD 12 can include any suitable blood pump (e.g., a centrifugal pump (as shown)) that is capable of pumping the entire output delivered to the left ventricle from the pulmonary circulation (i.e., up to 10 liters per minute). Related blood pumps applicable to the present invention are described in greater detail below and in U.S. Pat. Nos. 5,695,471, 6,071,093, 6,116,862, 6,186,665, 6,234,772, 6,264,635, 6,688,861, 7,699,586, 7,976,271, 7,997,854, 8,007,254, 8,152,493, 8,652,024, and 8,668,473 and U.S. Patent Publication Nos. 2007/0078293, 2008/0021394, 2009/0203957, 2012/0046514, 2012/0095281, 2013/0096364, 2013/0170970, 2013/0121821, and 2013/0225909, all of which are incorporated herein by reference for all purposes in their entirety. In the illustrated embodiment, the VAD 12 is attached to the heart 108 via the ventricular cuff 104, which can be sewn to the heart 108 and coupled to the VAD 12. In the illustrated embodiment, the VAD 12 pumps blood from the left ventricle of the patient's heart 108 to the ascending aorta via the outflow cannula 106 so that the VAD 12 effectively diverts blood from the weakened ventricle and propels it to the aorta for circulation through the rest of the patient's vascular system.

FIG. 2 illustrates the mechanical circulatory support system 10 during battery powered operation via the connected external battery module 16. Also, as described herein, the first patient interface module 14 and/or the second patient interface module 18 can include one or more battery cells to provide power for operating the VAD 12 in suitable circumstances, such as when sufficient power is not available from the external battery module 16. The percutaneous cable 20 exits through the patient's abdomen 110 and connects the VAD 12 to the first patient interface module 14, which is configured to control operation of the VAD 12 as described herein. Related controller systems applicable to the present invention are described in greater detail below and in U.S. Pat. Nos. 5,888,242, 6,991,595, 8,323,174, 8,449,444, 8,506,471, 8,597,350, and 8,657,733, EP 1812094, and U.S. Patent Publication Nos. 2005/0071001 and 2013/0314047, all of which are incorporated herein by reference for all purposes in their entirety. As described herein the mechanical circulatory assist system 10 can include any suitable number of the patient interface modules 14, 18.

Figure 3:
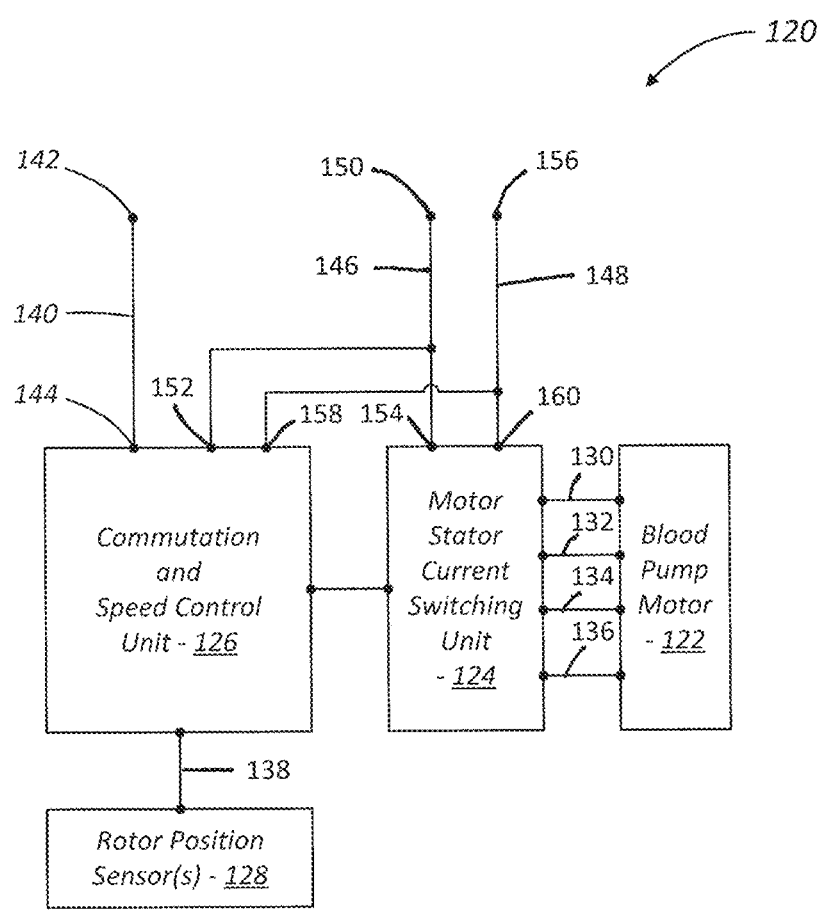
FIG. 3 is a simplified schematic diagram of a subassembly of a mechanical circulatory assist system that can be controlled by a patient interface module, in accordance with many embodiments.

FIG. 3 is a simplified schematic diagram of a subassembly 120 of a mechanical circulatory assist system that can be controlled by a patient interface module, such as any of the patient interface modules described herein. The subassembly 120 includes a blood pump motor 122, a motor stator current switching unit 124, a commutation and speed control unit 126, and one or more rotor position sensors 128. In the illustrated embodiment, the blood pump motor 122 includes three separate stator coils. Each of the stator coils is supplied current by the motor stator current switching unit 124 via a respective current supply line 130, 132, 134 and a ground line 136. Each of the respective current supply lines 130, 132, 134 and the ground line 136 can have one or more redundant back-up lines. In many embodiments, the ground line 130 includes two or more physically separated conductor lines. The motor stator current switching unit 124 is controlled by the commutation and speed control unit 126. The one or more rotor position sensors 128 generate one or more signals indicative of the position of a rotor of the blood pump motor 122 and supply the one or more rotor position signals to the commutation and speed control unit 126 via one or more signal lines 138 for use in controlling the motor stator current switching unit 124 based on the rotor position relative to the stator coils and one or more control parameters (e.g., target rotation speed) received via a control lead 140 connecting a control output 142 of a patient interface module with a control input 144 of the commutation and speed control unit 126. Electrical power is supplied to the subassembly 120 via a power lead 146 and a ground lead 148. The power lead 146 connects a power output 150 of the patient interface module with a power input 152 of the commutation and speed control unit 126 and a power input 154 of the motor stator current switching unit 124. The ground lead 148 connects a ground terminal 156 of the patient interface module with a ground terminal 158 of the commutation and speed control unit 126 and a ground terminal 160 of the motor stator current switching unit 124. In operation, power is supplied to the subassembly 120 via the power lead 146 and the ground lead 148 and the subassembly 120 controls operation of the blood pump motor 122 in accordance with one or more control parameters received from the patient interface module via the control lead 140.

Figure 4:
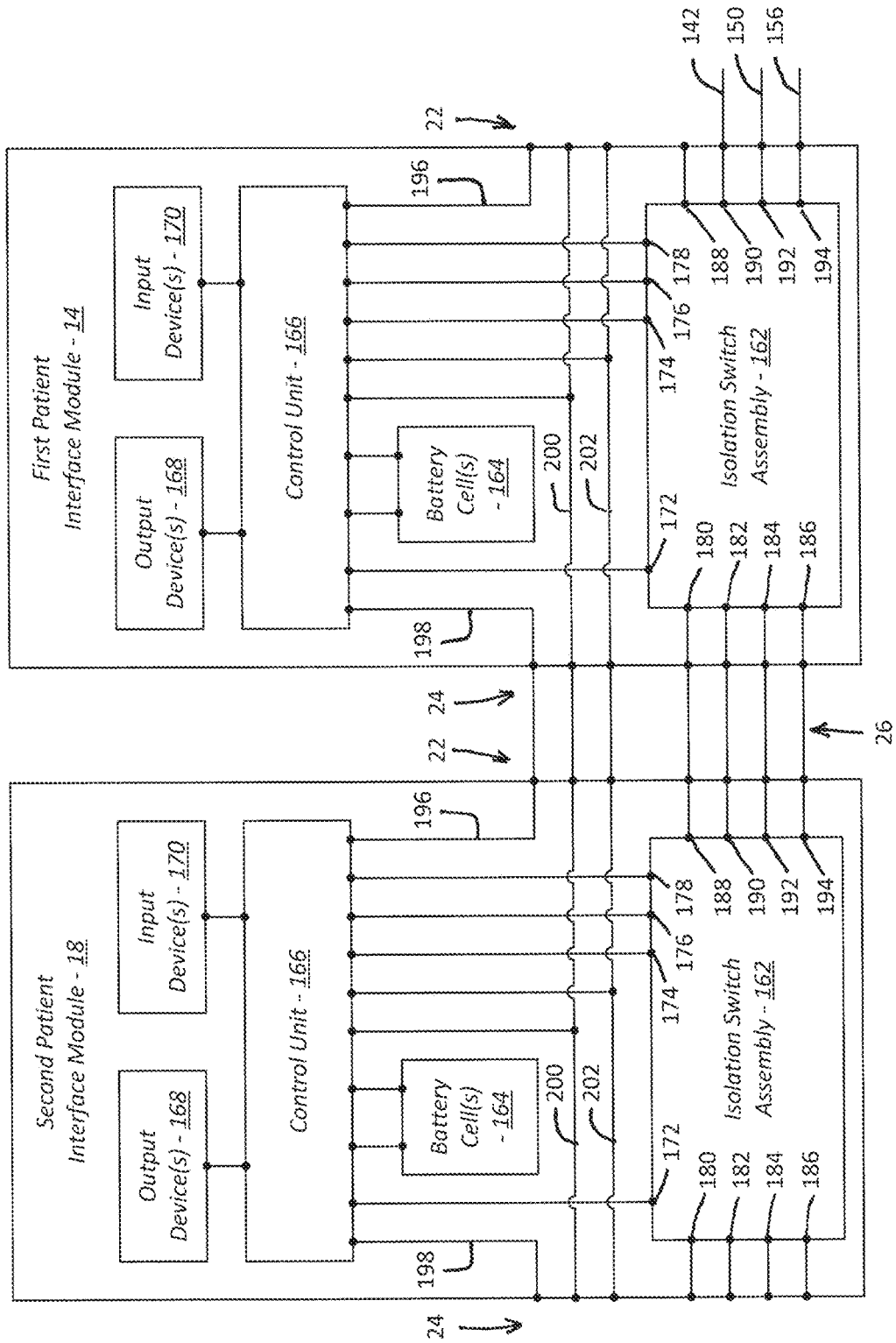
FIG. 4 is a simplified schematic diagram of an embodiment of the serially-connected patient interface modules of the mechanical circulatory assist system of FIG. 1 for controlling the mechanical circulatory assist system components of FIG. 3, in accordance with many embodiments.

FIG. 4 is a simplified schematic diagram of an embodiment of the serially-connected first and second patient interface modules 14, 18 of the mechanical circulatory assist system 10 for controlling the mechanical circulatory assist system subassembly 120 of FIG. 3, in accordance with many embodiments. Each of the first and second patient interface modules 14, 18 includes an isolation switch assembly 162, one or more battery cells 164, a control unit 166, one or more output devices 168, and one or more input devices 170.

The isolation switch assemblies 162 are controllable to operatively connect one of the patient interface modules to the subassembly 120 to control operation of the blood pump motor 122. The isolation switch assembly 162 includes inputs 172, 174, 176, 178 connected to the control module 166 of the patient interface module in which the isolation switch 162 is included. The isolation switch assembly 162 also includes inputs 180, 182, 184, 186 connected to the input connector 24 of the patient interface module in which the isolation switch 162 is included. The isolation switch assembly 162 includes outputs 188, 190, 192, 194 connected to the output connector 22 of the patient interface module in which the isolation switch 162 is included. The output 190 is connected to the control output 142. The input 172 is connected to the control unit 166 of the patient interface module in which the isolation switch assembly 162 is included and can transmit a switching control signal indicative of whether the patient interface module in which the isolation switch assembly 162 is included is functional to safely control operation of the subassembly 120. The input 180 can receive a control signal from an upstream serially connected patient interface module via the input connector 24. The control signal received via input 180 can be indicative of whether the upstream serially connected patient interface module is functional to safely control operation of the subassembly 120. Based on the control signal receive via the input 172 and the control signal received via the input 180, the isolation switch assembly 162 can operatively connect respective leads of the output connector 22 to the inputs 172, 174, 176, 178 or to the inputs 180, 182, 184, 186. Specifically, outputs 188, 190, 192, 194 are either connected to inputs 172, 174, 176, 178, respectively, or to inputs 180, 182, 184, 186, respectively. Accordingly, the control lead 142 is connected via the output 190 to either the control unit 166 of the patient interface module in which the isolation switch assembly 162 is included or via the input 182 to a control unit 166 of an upstream serially connected patient interface module.

In the illustrated embodiment, each of the patient interface modules 14, 18 includes an electrically-downstream connection lead 196 and an upstream connection lead 198 that provide a communication path over which negotiation between serially-connected patient interface modules can occur to determine which of the serially-connected patient interface modules will control the subassembly 120 (e.g., operate as a master in a master-slave control arrangement) and which of the serially-connected patient interface modules will operate in a standby mode (e.g., operate as a slave in the master slave-control arrangement). As illustrated in FIG. 4, the control unit 166 of the first patient interface module 14 is communicatively coupled with the control unit 166 of the second patient interface module 18 via the upstream connection lead 198 of the first patient interface module 14, the input connector 24 of the first patient interface module 14, the connection cable 26, the output connector 22 of the second patient interface module 18, and the downstream connection lead 196 of the second patient interface module. In many embodiments, each of the control units 166 is configured to sense when other patient interface module is connected and to negotiate which one of the patient interface modules will control the subassembly 120 and which will operate in a standby mode. Each of the control units 166 can communicate the functional status of the patient interface module and the selection of which patient control unit controls the subassembly 120 can be based on the functional status and/or connection order using any suitable approach. For example, where both of the first and second patient interface modules 14, 18 are in a fully functional state, either of the first and second patient interface modules 14, 18 can be selected to control operation of the subassembly 120. Where only one of the patient interface modules 14, 18 is fully functional, the fully functional patient interface module can be selected to control operation of the subassembly 120. Based on the results of the negotiation, the control units 166 can control operation of the isolation switch assembly 162 via control signals via inputs 172, 180 to operatively connect the selected patient interface assembly to the subassembly 120. In some embodiments, the downstream connection lead 196 and the upstream connection lead 198 are replaced by pass-through wires forming a common communication bus, with a communication protocol established for two more patient interface modules to time-share the common bus. In some embodiments, downstream connection lead 196 and the upstream connection lead 198 are implemented alongside pass-through wires forming a common communication bus. Any suitable common communication bus can be employed (e.g., a standardized internal communication network such as a controller area network (CAN bus)).

In a similar fashion, the isolation switch assembly 162 of the second patient interface module 18 is operable to switch connection of the output 190 to be connected to the input 174, which is connected to the control unit 166 of the second patient interface module 18, or to the input 182, which can be connected to the output 190 of an upstream patient interface module. Accordingly, the control lead 142 can be operatively coupled with any one of two or more serially-connected patient interface modules via control of the isolation switch assemblies 162.

Each of the patient interface modules 14, 18 is configured to receive and output battery power via a pass-through bus power lead 200 and a pass-through bus ground lead 202. The power lead 200 and the ground lead 202 in serially connected control modules are connected via the respective input connector(s) 24 and output connector(s) 22. The control unit 166 is connected to the power leads 200, 202. In many embodiments, the control unit 166 is configured to supply power to the subassembly 120 via power received from the power leads 200, 202, and from the battery cell(s) 164 if sufficient power is not available via the power leads 200, 202. The control unit 166 can also be configured to use power received from the power leads 200, 202 to charge the battery cell(s) 164 if the battery cell(s) are not already fully charged. In many embodiments, the control unit 166 is configured to control transmission of power to the subassembly 120 via the power output 150 and ground terminal 156, which can be operatively connected with the inputs 176, 178 of the isolation switch assembly 162 as described herein.

Figure 5:
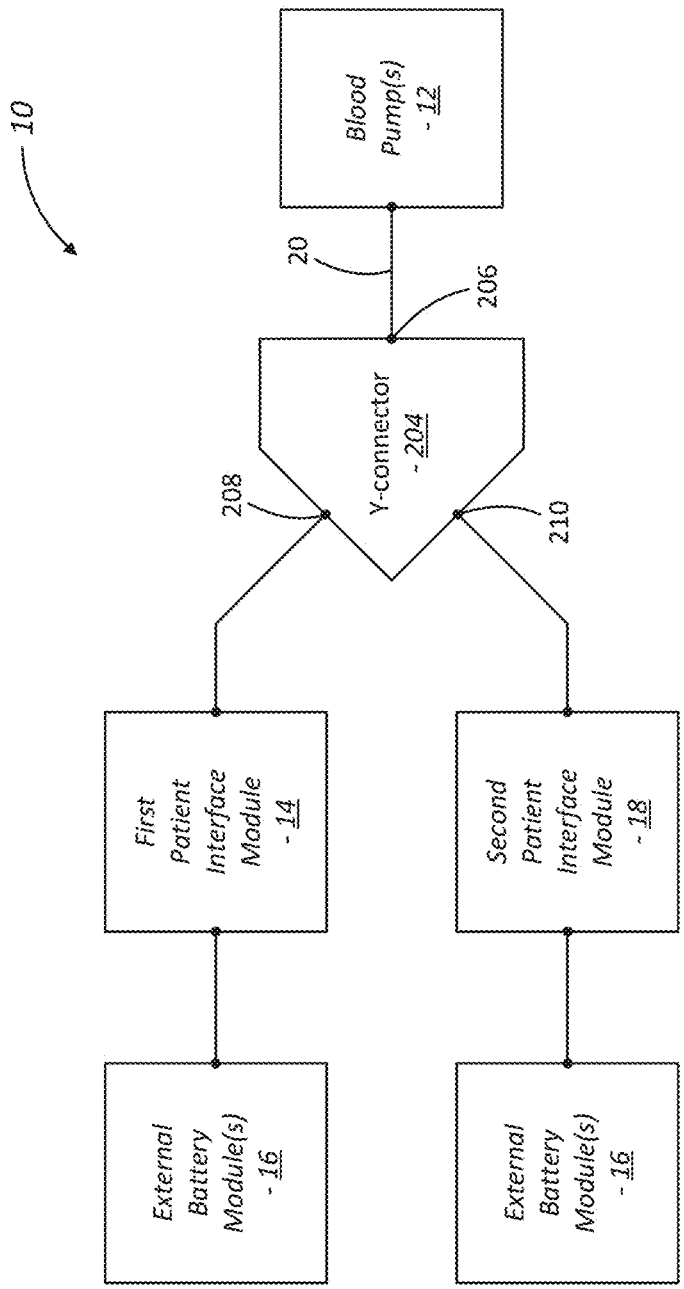
FIG. 5 is a simplified schematic diagram of a mechanical circulatory assist system in which a plurality of patient interface modules can be connected via a Y-connector, in accordance with many embodiments.

FIG. 5 is a simplified schematic diagram of an embodiment of the mechanical circulatory assist system 10 in which the plurality of patient interface modules 14, 18 can be connected via a Y-connector 204, in accordance with many embodiments. In the illustrated embodiment, the Y-connector 204 includes an output 206 that is connected to the proximal end of the percutaneous cable 20. The Y-connector 204 includes a first input connector 208 to which the first patient interface module 14 can be connected and a second input connector 210 to which the second patient interface module 18 can be connected.

The Y-connector 204 is configured to accommodate the physical coupling of one and two patient interface modules to the blood pump(s) 12 (e.g., to the subassembly 120) and to operatively couple one of the patient interface modules to the blood pump(s) 12. The Y-connector 204 can have any suitable configuration. For example, the Y-connector 204 can include any suitable switching elements (mechanical, electronic, and/or software) for operatively coupling the output 206 to either one of the input connector 208 or the output connector 210. In some embodiments, the Y-connector 204 is configured to, upon connection of a patient interface module to the second input connector 210, operatively decouple output 206 from the first input connector 208 and operatively couple the output 206 to the second input connector 210. In many embodiments, the first input connector 208 and/or the second input connector 210 include a locking mechanism that is configured to inhibit or prevent decoupling of the patient interface module from the input connector by the patient and to require specialized equipment and/or methodology to decouple the patient interface module so as to ensure that the patient interface module is only decoupled by a suitable health care professional.

The Y-connector 204 can include features suitable to a blood pump that is supplied an alternating current from the patient interface modules 14, 18. The Y-connector 204 can include a phase-sensing circuit configured to sense a phase of the alternating current supplied by the respective patient interface module to the blood pump. Each of the first and second patient interface modules can be configured to, upon assuming control of the blood pump from the other of the first and second patient interface modules, receive a signal from the Y-connector 204 indicative of the phase of the alternating current that was supplied to the blood pump and supply an alternating current to the blood pump having the same phase.

Figure 6:
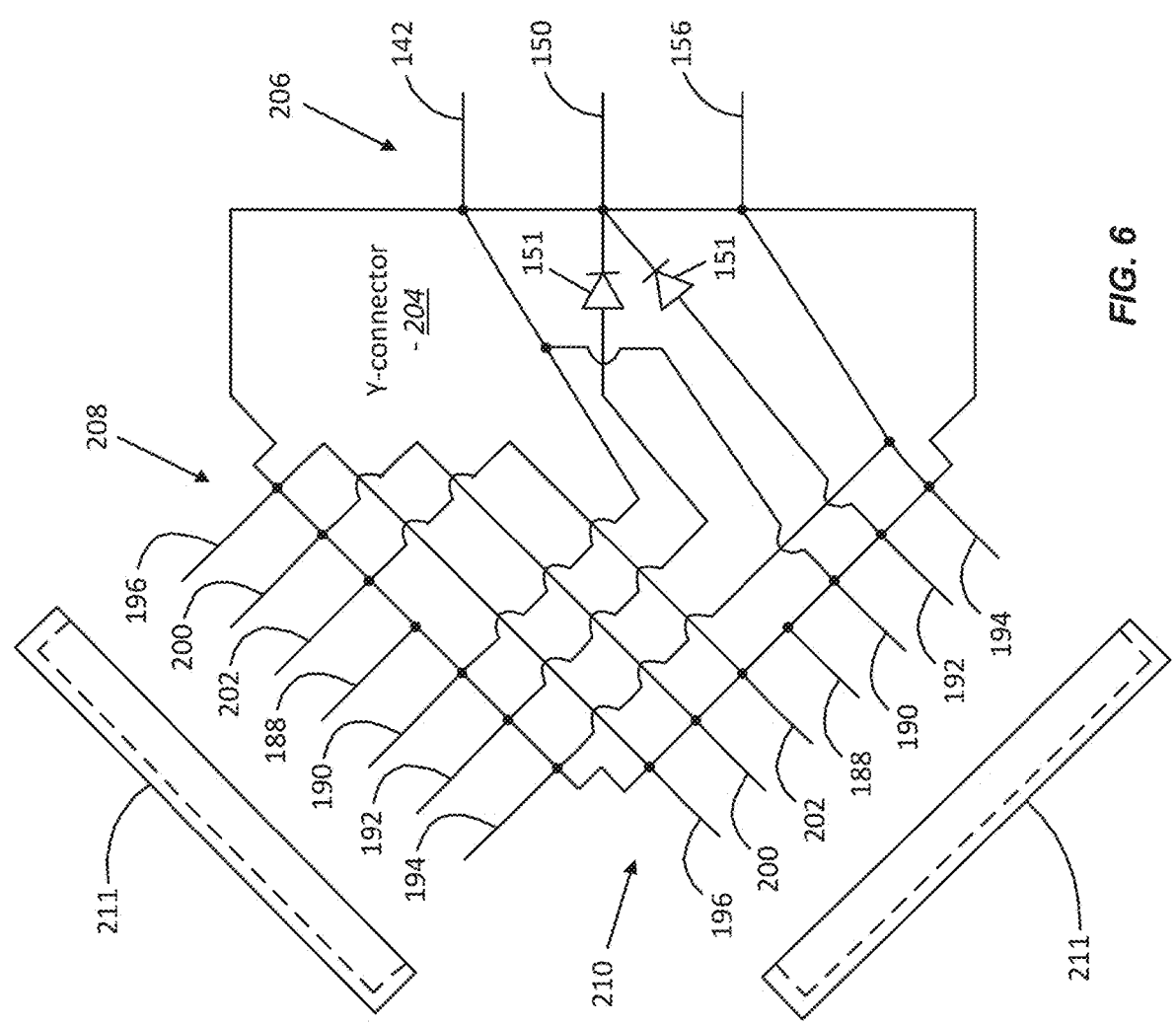
FIG. 6 is a simplified schematic diagram of an embodiment of the Y-connector of FIG. 5.

FIG. 6 is a simplified schematic diagram of an embodiment of the Y-connector 204. In the illustrated embodiment, the Y-connector 204 is configured similar to the isolation switch assembly 162 described herein but further includes the pass-through bus power lead 200, the pass-through bus ground lead 202, and diodes 151, each of which is connected between a respective power input 190 and the power output 150 to prevent back driving of current from one of the power inputs 190 to the other of the power inputs 190. The above descriptions of the isolation switch assembly 162, the pass-through bus power lead 200, and the pass-through bus ground lead 202 are applicable to the Y-connector 204 and are not repeated here. Each of the patient interface modules 14, 18 can separately include a diode 151 that is integrated to prevent back driving of current into the patient interface module from the power output 190 of the other controller.

In many embodiments, the Y-connector 204 is part of an assembly that includes one or more input connector covers 211 for protecting the first input connector 208 and/or the second input connector 210 from fluid ingress and/or contaminants when the input connector 208, 210 is not connected with a patient interface module 14, 18 or an external battery module 16. The input connector cover 211 can have any suitable configuration for blocking fluid ingress and/or contaminants. For example, the input connector cover 211 can be configured to be reusable so that the patient can demount the input connector cover 211 from the Y-connector 204 to uncover the input connector 208, 210 for connection with a patient interface module 14, 18 or an external battery module 16 and so that the patient can mount the input connector cover 211 to cover the input connector 208, 210 when the input connector 208, 210 is not in use and thereby protect the input connector 208, 210 from fluid ingression and/or other contaminants. The Y-connector 204 can be equipped with a single use input connector cover 211 mounted to a currently unused one of the input connectors 208, 210 with the single use input connector cover 211 being removable by the patient. The input connector cover 211 can include a thin film that blocks ingress of fluid and/or contaminants into the input connector 208, 210. The thin film can be removable to accommodate connection of a patient interface module 14, 18 or an external battery module 16 with the input connector 208, 210. The thin film can be configured to be pierced via connection of a patient interface module 14, 18 or an external battery module 16 with the input connector 208, 210.

Figure 7:
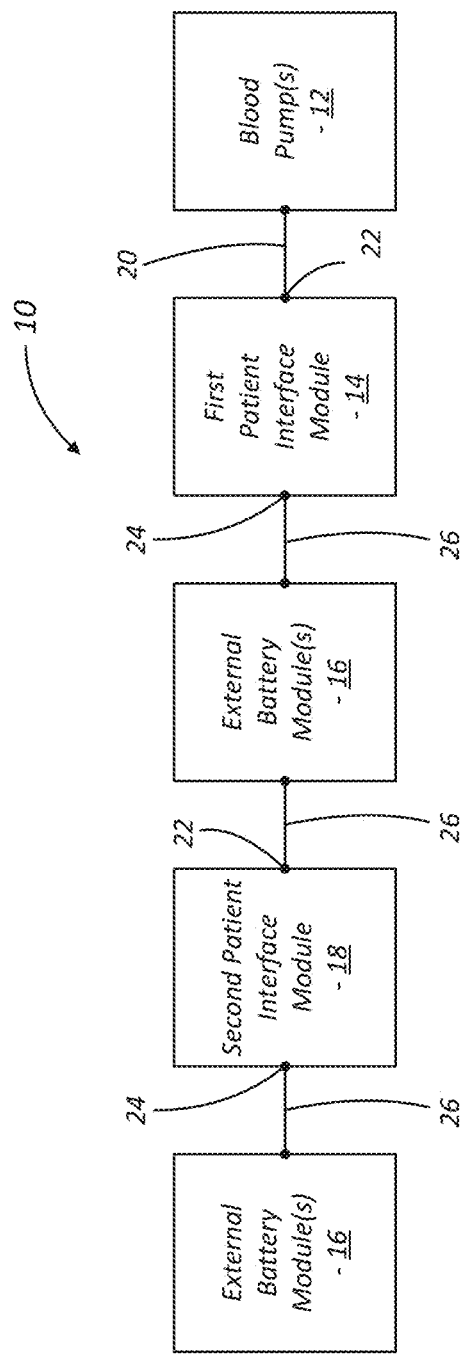
FIG. 7 is a simplified schematic diagram of a mechanical circulatory assist system in which a plurality of patient interface modules and one or more external battery modules can be connected serially, in accordance with many embodiments.

FIG. 7 is a simplified schematic diagram of an embodiment of the mechanical circulatory assist system 10 in which the plurality of patient interface modules 14, 18 and one or more of the external battery modules 16 can be connected in series, in accordance with many embodiments. The illustrated embodiment is similar to the embodiment illustrated in FIG. 1, but the external battery module(s) 16 are configured to be serially connected with the patient interface modules 14, 18. For example, in the illustrated configuration, one external battery module 16 is shown coupled to the input connector 24 of the first patient interface module 14 via a connection cable 26 and to the output connector 22 of the second patient interface module 18 via another connection cable 26. Another external battery module 16 is shown coupled to the input connector 24 of the second patient interface module 18 via another connection cable 26. While FIG. 7 shows two patient interface modules 14, 18 and two external battery modules 16 serially connected in a particular order, any suitable number of the patient interface modules and any suitable number of the external battery modules 16 can be connected in any suitable order. For example, one or more additional external battery modules 16 can be connected between the first patient interface module 14 and the second patient interface module 18. As another example, one or more additional external battery modules 16 can serially connected to the external battery module 16 connected to the input connector 24 of the second patient interface module 18.

Figure 8:
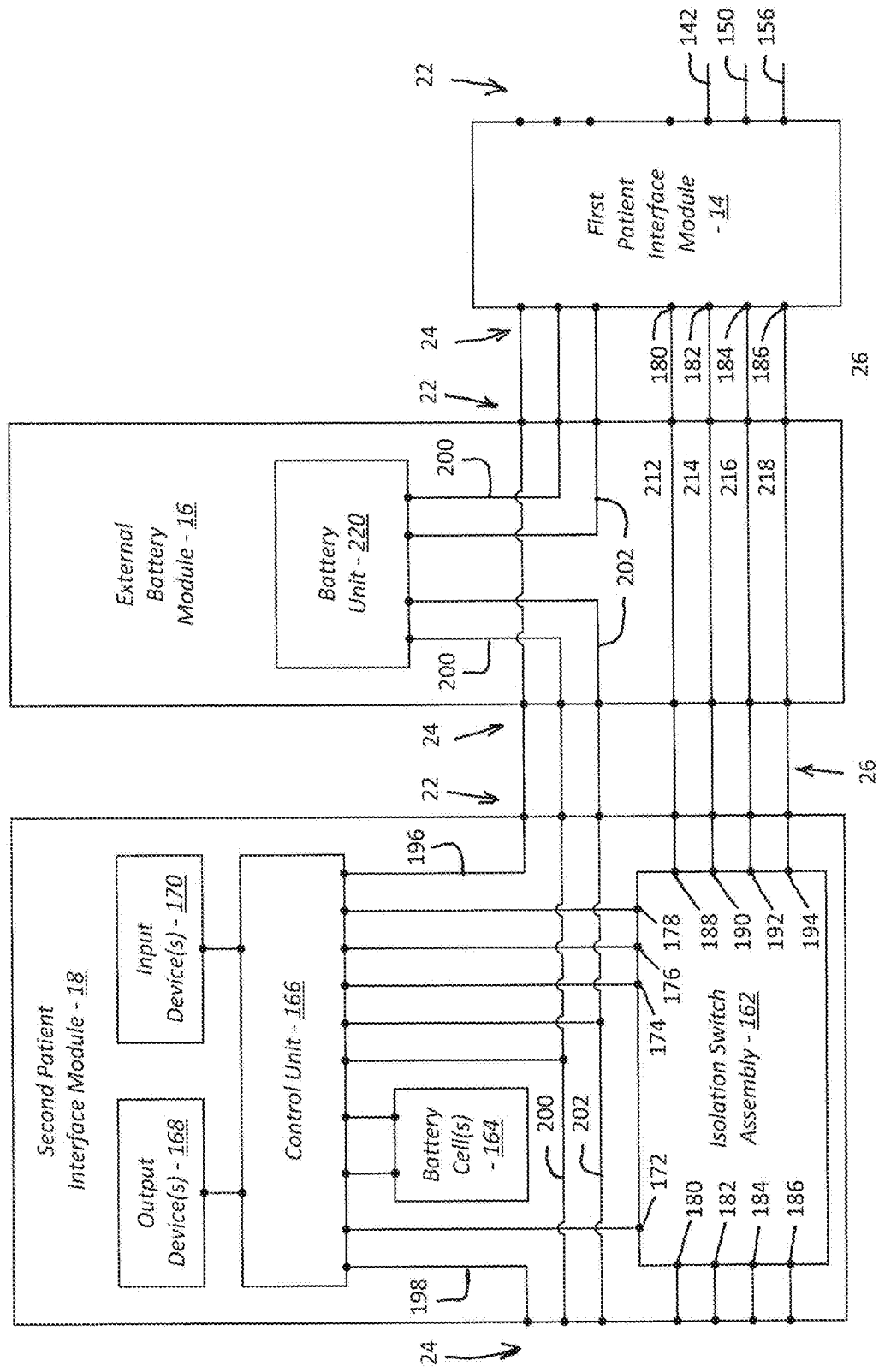
FIG. 8 is a simplified schematic diagram of an embodiment of the serially-connected patient interface modules and an external battery module of the mechanical circulatory assist system of FIG. 7 for controlling the mechanical circulatory assist system components of FIG. 3, in accordance with many embodiments.

FIG. 8 is a simplified schematic diagram of an embodiment of the serially-connected patient interface modules 14, 18 and an external battery module 16 of the mechanical circulatory assist system of FIG. 7 for controlling the subassembly 120 of FIG. 3, in accordance with many embodiments. The first and second patient interface modules 14, 18 are described above with reference to FIG. 4. The external battery module 16 includes an output connector 22 and an input connector 24 configured the same as the output and input connectors 22, 24 of the first and second patient interface modules 14, 18. The external battery module includes pass-through connection lines 212, 214, 216, 218 that connect respective connections in the output and input connectors 22, 24. Connection line 212 connects output 188 of the second patient interface module 18 with input 180 of the first patient interface module. Connection line 214 connects output 190 of the second patient interface module 18 with input 182 of the first patient interface module. Connection line 212 connects output 192 of the second patient interface module 18 with input 184 of the first patient interface module. Connection line 212 connects output 194 of the second patient interface module 18 with input 186 of the first patient interface module.

The external battery module 16 includes a battery unit 220 to which the pass-through bus power lead 200 and the pass-through bus ground lead 202 are connected. The battery unit 220 is configured to output power from the output connector 22 via the power lead 200 and the ground lead 202 connecting the battery unit 220 to the output connector 22. The power output by the battery unit 220 can be received via the power lead 200 and the ground lead 202 connected to the input connector 24 and/or from one or more battery cells included in the battery unit 22. In many embodiments, where power is received by the battery unit 220 over the power lead 200 and the ground lead 202 connecting the battery unit 220 to the input connector 24, the battery unit 220 can use any suitable portion of the received power to charge the one or more battery cells included in the battery unit 220 if the one or more battery cells are not already fully charged.

Figure 9:
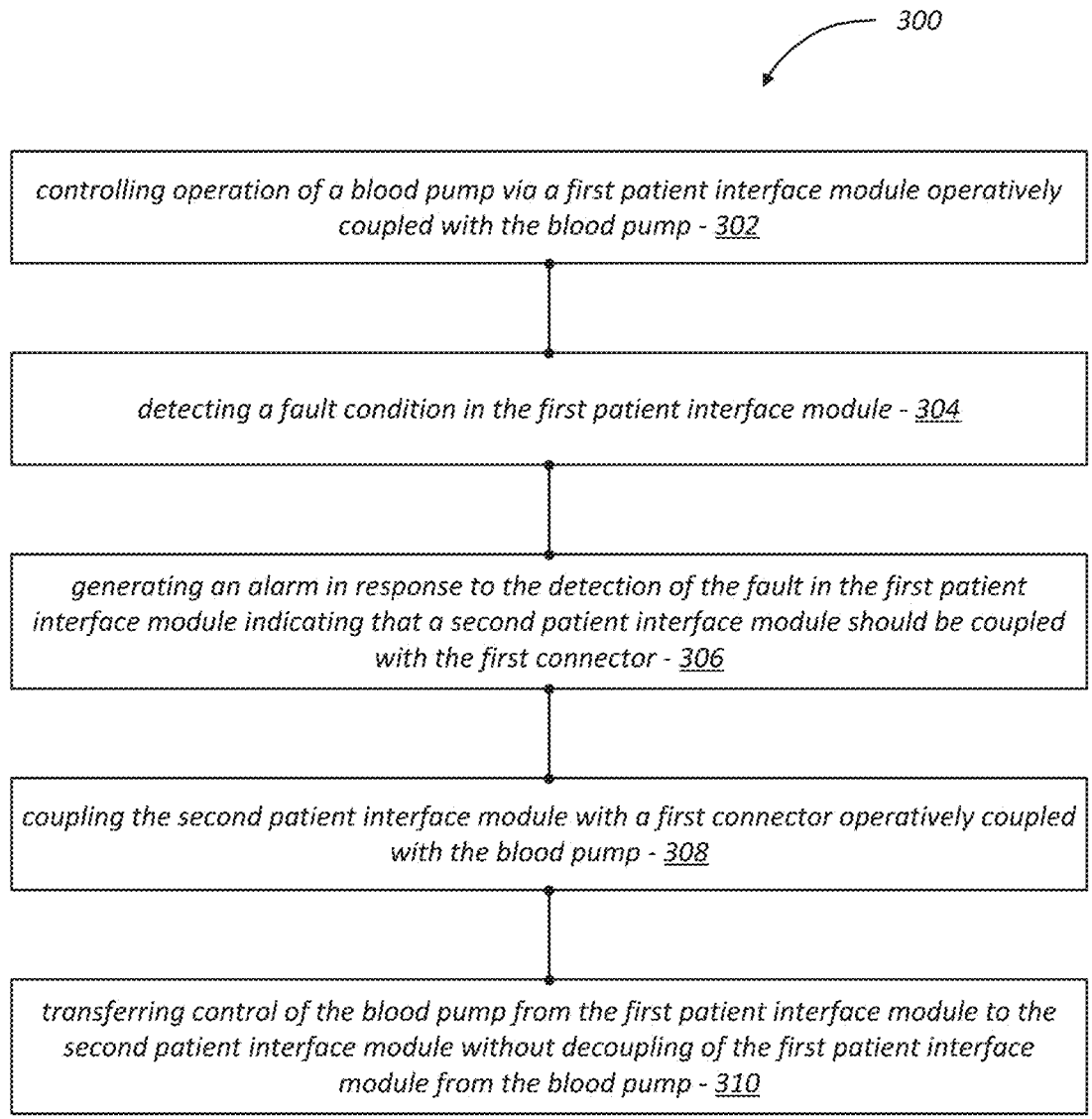
FIG. 9 is a simplified schematic diagram of acts of a method for controlling a mechanical circulatory assist system, in accordance with many embodiments.

FIG. 9 is a simplified schematic diagram of acts of a method 300 for controlling a mechanical circulatory assist system, in accordance with many embodiments. Any suitable mechanical circulatory assist system, such as any suitable mechanical circulatory assist system described herein, can be used to practice the method 300. The method 300 includes controlling operation of a blood pump via a first patient interface module operatively coupled with the blood pump (act 302), detecting a fault condition in the first patient interface module (act 304), generating an alarm in response to the detection of the fault in the first patient interface module indicating that a second patient interface module should be coupled with a first connector operatively coupled with the blood pump (act 306), coupling the second patient interface module with a first connector operatively coupled with the blood pump (act 308), and transferring control of the blood pump from the first patient interface module to the second patient interface module without decoupling of the first patient interface module from the blood pump (act 310).

Figure 10:
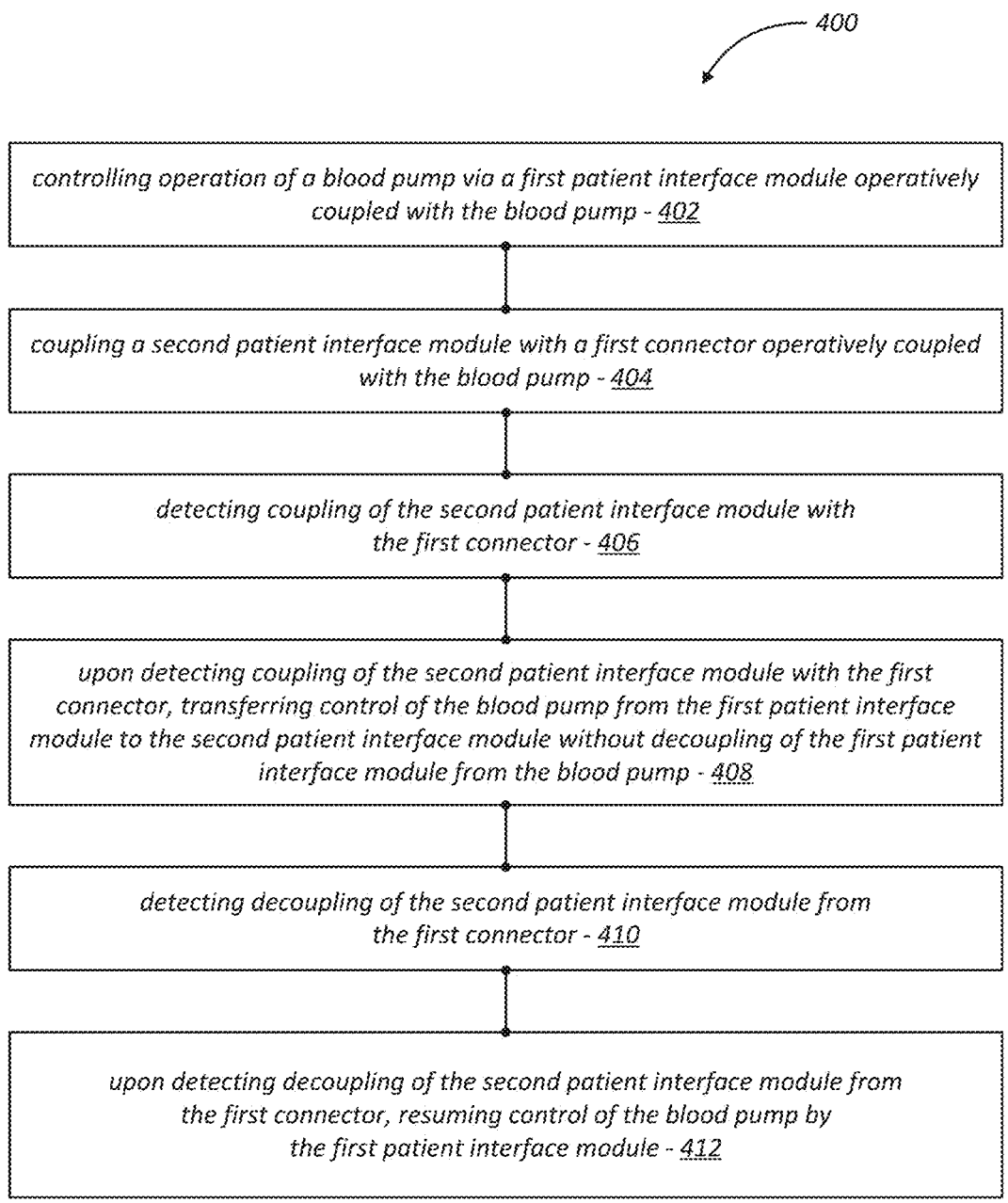
FIG. 10 is a simplified schematic diagram of acts of a method for controlling a mechanical circulatory assist system, in accordance with many embodiments.

FIG. 10 is a simplified schematic diagram of acts of a method 400 for controlling a mechanical circulatory assist system, in accordance with many embodiments. Any suitable mechanical circulatory assist system, such as any suitable mechanical circulatory assist system described herein, can be used to practice the method 400. The method 400 includes controlling operation of a blood pump via a first patient interface module operatively coupled with the blood pump (act 402); coupling a second patient interface module with a first connector operatively coupled with the blood pump (act 404); detecting coupling of the second patient interface module with the first connector (act 406); upon detecting coupling of the second patient interface module with the first connector, transferring control of the blood pump from the first patient interface module to the second patient interface module without decoupling of the first patient interface module from the blood pump (act 408); detecting decoupling of the second patient interface module from the first connector (act 410); and upon detecting decoupling of the second patient interface module from the first connector, resuming control of the blood pump by the first patient interface module (act 412).

Figure 11:
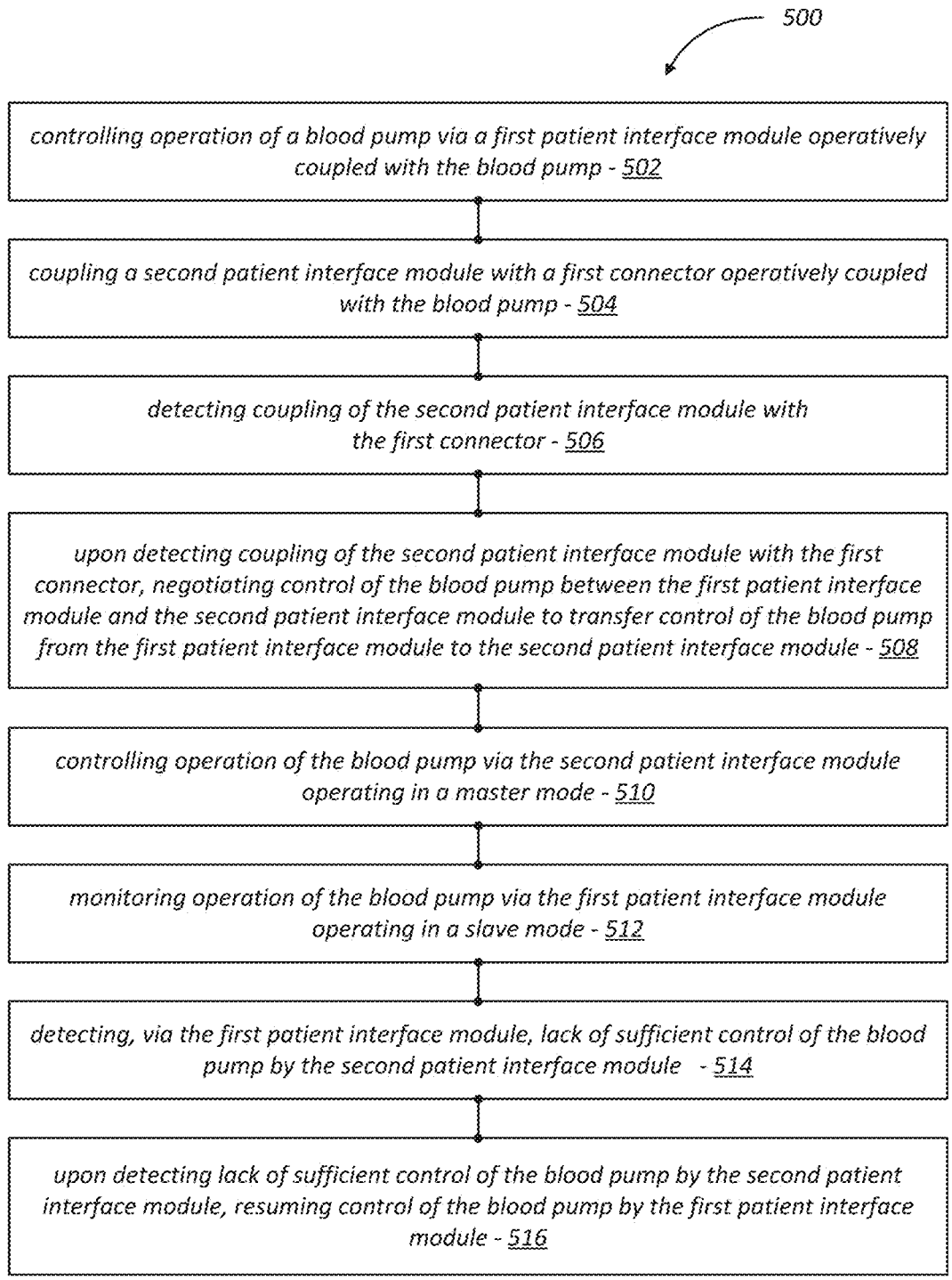
FIG. 11 is a simplified schematic diagram of acts of a method for controlling a mechanical circulatory assist system, in accordance with many embodiments.

FIG. 11 is a simplified schematic diagram of acts of a method 500 for controlling a mechanical circulatory assist system, in accordance with many embodiments. Any suitable mechanical circulatory assist system, such as any suitable mechanical circulatory assist system described herein, can be used to practice the method 500. The method 500 includes controlling operation of a blood pump via a first patient interface module operatively coupled with the blood pump (act) 502; coupling a second patient interface module with a first connector operatively coupled with the blood pump (act 504); detecting coupling of the second patient interface module with the first connector (act 506); upon detecting coupling of the second patient interface module with the first connector, negotiating control of the blood pump between the first patient interface module and the second patient interface module to transfer control of the blood pump from the first patient interface module to the second patient interface module (act 508); controlling operation of the blood pump via the second patient interface module operating in a master mode (act 510); monitoring operation of the blood pump via the first patient interface module operating in a slave mode (act 512); detecting, via the first patient interface module, lack of sufficient control of the blood pump by the second patient interface module (act 514); and upon detecting lack of sufficient control of the blood pump by the second patient interface module, resuming control of the blood pump by the first patient interface module (act 516).

In embodiments described herein in which the patient interface modules include one or more battery cells, the user of the mechanical circulatory assist system can manage battery life by connecting and disconnecting patient interface modules and/or external battery modules. Such routine connection and disconnection of patient interface modules thereby becomes part of the user's daily life and may vastly boost the user's proficiency in dealing with a faulty patient interface module.

Also, because several patient interface modules can be connected simultaneously, the user of the mechanical circulatory assist system never has to remove one patient interface module before connecting a replacement patient interface module. Not having to disconnect a patient interface module before connecting a replacement patient interface module saves time and also means the user does not have to go completely without a patient interface module when "replacing" a patient interface module that still has some functionality. The "replaced" patient interface module can later be removed from the system under non-urgent conditions by trained staff at a clinic.

Any suitable approach can be used to couple a replacement patient interface module to an already connected patient interface module. For example, the replacement patient interface module may be connected to another module either directly (direct physical contact), or through a cable.

In embodiments including a Y-connector, any suitable approach can be used with regard to connection of one or more patient interface modules. For example, the user can regularly use the same, single patient interface module connected to one port on the Y-connector and leaves the other port free. The user can then connect another module to the free port of the Y-connector when instructed to do so by an alarm. As another example, the user can regularly use two patient interface modules thereby using both ports on the Y-connector. The user can use two connected patient interface modules to extend total battery capacity to extend run time. The user can also disconnect and charge one of the two patient interface modules while operating with the other patient interface module or to cycle through three or more patient interface modules to gain extended run-time or for patient interface module charging. In embodiments including the Y-connector, the patient interface module(s) can include or exclude an input connector for connecting another patient interface module. Additionally, a patient interface module can include more than one input connectors, thereby accommodating the connection of more than one patient interface module to the patient interface module.

The systems and approaches described herein can be used in conjunction with patient interface modules that provide alternating current (AC) power to the blood pump(s). In such embodiments, each patient interface module can include a phase-sensing circuit and the patient interface modules can be configured so that the replacement patient interface module supplies alternating current that matches the phase of the alternating current provided by the "replaced" patient interface module.

Connectors/receptacles to which patient interface modules are connected can be fitted with mechanical isolation elements, so that the original patient interface module is isolated from the percutaneous lead when the replacement patient interface module is mechanically connected (possibly via a connection cable) to the originally connected patient interface module. In embodiments that include the Y-connector, the originally connected patient interface module can be isolated from the percutaneous lead when the replacement patient interface module is mechanically connected (possible via a connection cable) to the Y-connector. In other words, the Y-connector can be configured to mechanically allow only one module to be electrically connected to the blood pump at a time.

The patient interface modules can be fitted with electrical isolation elements configured so that only one patient interface module is operatively connected with the blood pump(s). For example, the originally connected patient interface module can include a circuit that can identify when a replacement patient interface module is electrically connected and shuts down the originally connected patient interface module (e.g., shut down to a sleep mode with sufficient monitoring function to wake up if the replacement patient interface module is disconnected or malfunctions). In some embodiments, the patient interface module furthest away from the blood pump in the sequential chain can be designated master while any other patient interface modules on the sequential chain can be slaves (active or in sleep mode).

The patient interface modules can include software and algorithms that determine based on communications data how many patient interface modules are connected and which of the connected patient interface modules should shut down (sleep mode with sufficient monitoring function to wake up if the other module is disconnected or malfunctions) and which should stay active.

As describe herein, a mix of patient interface modules and external battery modules can be employed. In such embodiments, the patient interface modules may or may not have internal battery cells. In such embodiments, each patient interface module can be configured to send at least two different alerts to the user to take action, for example: "replace power source" and "replace module." In some embodiments in which the same connectors are used in the patient interface modules and the external battery modules, the user receives the same training benefit when replacing external battery modules as for replacing patient interface modules because the replacement appears similar to the user.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A mechanical circulatory assist system, comprising:
    a blood pump configured for implantation in a patient;
    a percutaneous cable having a proximal end and a distal end, wherein the distal end is connected with the blood pump, and wherein the percutaneous cable is configured to be partially implanted in the patient to extend through the patient's abdomen to dispose the distal end within the patient and the proximal end external to the patient;
    an external connector connected to the percutaneous cable, wherein the external connector comprises an external connector first input connector and an external connector second input connector;
    a first patient interface module configured to control operation of the blood pump, wherein the first patient interface module comprises a first patient interface module output connector configured to be connected to the external connector first input connector to operatively couple the first patient interface module with the blood pump for control of operation of the blood pump by the first patient interface module; and
    a second patient interface module configured to control operation of the blood pump, wherein the second patient interface module comprises a second patient interface module output connector configured to be connected to the external connector second input connector to operatively couple the second patient interface module with the blood pump for control of operation of the blood pump by the second patient interface module,
    wherein the second patient interface module output connector is configured be connected to the external connector second input connector while the first patient interface module output connector is connected to the external connector first input connector to reconfigure from a decoupled configuration in which the second patient interface module output connector is decoupled from the external connector second input connector.

2. The mechanical circulatory assist system of claim 1, wherein the first patient interface module is configured to:
    detect a fault in the first patient interface module;
    generate an alarm in response to the detection of the fault in the first patient interface module indicating that the second patient interface module should be coupled with the external connector; and
    relinquish control of the blood pump to the second patient interface module.

3. The mechanical circulatory assist system of claim 2, wherein the first patient interface module comprises one or more output devices for outputting the alarm.

4. The mechanical circulatory assist system of claim 1, wherein the external connector is configured to, upon connection of the second patient interface module output connector to the external connector second input connector, operatively decouple the external connector first input connector from the blood pump and operatively couple the external connector second input connector with the blood pump.

5. The mechanical circulatory assist system of claim 1, further comprising:
    a motor stator current switching unit operable to control supply of current to stator coils of a blood pump motor of the blood pump; and
    a commutation and speed control unit configured to control operation of the motor stator current switching unit in accordance with one or more control parameters transmitted over the percutaneous cable by either of the first patient interface module or the second patient interface module.

6. The mechanical circulatory assist system of claim 5, wherein each of the first patient interface module and the second patient interface module is configured to receive electrical power from a respective power source and direct the electrical power over the percutaneous cable to the motor stator current switching unit.

7. The mechanical circulatory assist system of claim 1, wherein each of the first patient interface module and the second patient interface module is configured to supply current to stator coils of a blood pump motor of the blood pump through the percutaneous cable.

8. A method of controlling a mechanical circulatory assist system that includes a blood pump, the method comprising:
    controlling operation of a blood pump implanted within a patient by a first patient interface module operatively coupled with the blood pump by a percutaneous cable and an external connector disposed external to the patient, wherein the percutaneous cable is connected with the blood pump, wherein the external connector is connected to the percutaneous cable, and wherein the first patient interface module is connected to external connector;
    coupling a second patient interface module with the external connector while the first patient interface module is coupled with the external connector to reconfigure from a decoupled configuration in which the second patient interface module is decoupled from the external connector; and
    transferring control of the blood pump from the first patient interface module to the second patient interface module without decoupling of the first patient interface module from the external connector.

9. The method of claim 8, further comprising:
    detecting a fault condition in the first patient interface module; and
    generating an alarm in response to the detection of the fault in the first patient interface module indicating that the second patient interface module should be coupled with the external connector.

10. The method of claim 8, further comprising:
    detecting coupling of the second patient interface module with the external connector; and
    upon detecting coupling of the second patient interface module with the external connector, transferring control of the blood pump from the first patient interface module to the second patient interface module.

11. The method of claim 10, further comprising:
    detecting decoupling of the second patient interface module from the external connector; and upon detecting decoupling of the second patient interface module from the external connector, resuming control of the blood pump by the first patient interface module.

12. The method of claim 8, further comprising:
coupling a third patient interface module to a second connector operatively coupled with the blood pump; and
transferring control of the blood pump from the second patient interface module to the third patient interface module without decoupling at least one of the first and second patient interface modules from the blood pump.

13. The method of claim 12, the method further comprising detecting a fault condition in the second patient interface module.

14. The method of claim 13, further comprising generating an alarm in response to the detection of the fault in the second patient interface module indicating that the third patient interface module should be coupled with the second connector.

15. The method of claim 8, further comprising supplying electrical power to the blood pump from one or more battery cells coupled with the second patient interface module.

16. The method of claim 8, wherein transferring control of the blood pump from the first patient interface module to the second patient interface module without decoupling of the first patient interface module from the blood pump comprises negotiating control of the blood pump between the first and second patient interface modules so that the second patient interface module functions as a master that controls the operation of the blood pump and the first patient interface module functions as a slave that does not control the operation of the blood pump.

17. The method of claim 8, wherein:
the external connector comprises an external connector first input connector and an external connector second input connector;
the first patient interface module comprises a first patient interface module output connector configured to be connected to the external connector first input connector to operatively couple the first patient interface module with the blood pump for control of operation of the blood pump by the first patient interface module; and
the second patient interface module comprises a second patient interface module output connector configured to be connected to the external connector second input connector to operatively couple the second patient interface module with the blood pump for control of operation of the blood pump by the second patient interface module.

18. The method of claim 17, further comprising negotiating control of the blood pump between the first and second patient interface modules so that one of the first and second patient interface modules functions as a master that controls the operation of the blood pump and the other of the first and second patient interface modules functions as a slave that does not control the operation of the blood pump.

19. The method of claim 17, wherein coupling the second patient interface module to the external connector operatively decouples the first patient interface module from the blood pump.

20. The method of claim 8, further comprising transferring electrical power from an external battery module coupled with one of the first and second patient interface modules.

21. The method of claim 8, further comprising activating a lock upon coupling of the second patient interface module with the external connector to prevent decoupling of the second patient interface module from the external connector by a person other than a qualified person.

22. The method of claim 21, wherein the lock is activated at least one of mechanically, electrically, or through software.

23. A method of controlling a mechanical circulatory assist system that includes a blood pump, the method comprising:
controlling operation of the blood pump via a first patient interface module operatively coupled with the blood pump;
coupling a second patient interface module with a first connector operatively coupled with the blood pump;
transferring control of the blood pump from the first patient interface module to the second patient interface module without decoupling of the first patient interface module from the blood pump;
supplying a first alternating current from the first patient interface module to the blood pump;
sensing a phase of the first alternating current; and
supplying a second alternating current from the second interface module to the blood pump so that a phase of the second alternating current matches the phase of the first alternating current.

* * * * *